US012623208B2

(12) United States Patent  
Asefa et al.

(10) Patent No.: US 12,623,208 B2  
(45) Date of Patent: May 12, 2026

(54) TITANIUM DIOXIDE PARTICLES AND METHODS OF MAKING THE SAME

(71) Applicants: Rutgers, The State University of New Jersey, New Brunswick, NJ (US); Institute of Scientific Instruments of the Czech Academy of Sciences, v.v.i., Brno (CZ)

(72) Inventors: Tewodros Asefa, Piscataway, NJ (US); Tao Zhang, Piscataway, NJ (US); Eliška Materna Mikmeková, Brno (CZ); Alexei M. Tyryshkin, Piscataway, NJ (US)

(73) Assignees: Rutgers, The State University of New Jersey, New Brunswick, NJ (US); Institute of Scientific Instruments of the Czech Academy of Sciences, v.v.i., Brno (CZ)

( * ) Notice: Subject to any disclaimer, the term of this patent is extended or adjusted under 35 U.S.C. 154(b) by 690 days.

(21) Appl. No.: 17/925,372

(22) PCT Filed: May 14, 2021

(86) PCT No.: PCT/US2021/032469  
§ 371 (c)(1),  
(2) Date: Nov. 15, 2022

(87) PCT Pub. No.: WO2021/231878  
PCT Pub. Date: Nov. 18, 2021

(65) Prior Publication Data  
US 2023/0191370 A1     Jun. 22, 2023

Related U.S. Application Data

(60) Provisional application No. 63/025,225, filed on May 15, 2020.

(51) Int. Cl.  
*B01J 21/06* (2006.01)  
*B01J 35/39* (2024.01)  
(Continued)

(52) U.S. Cl.  
CPC ............. *B01J 21/063* (2013.01); *B01J 35/39* (2024.01); *B01J 35/45* (2024.01); *B01J 35/613* (2024.01);  
(Continued)

(58) Field of Classification Search  
CPC . B01J 21/063; B01J 35/39; B01J 35/45; B01J 35/613; B01J 35/615; B01J 35/633; B01J 35/647; C07C 1/12  
See application file for complete search history.

(56) References Cited

U.S. PATENT DOCUMENTS

2009/0286676 A1     11/2009  Kim et al.  
2012/0160695 A1     6/2012  Misra et al.  
(Continued)

FOREIGN PATENT DOCUMENTS

JP        2010120800 A     6/2010  
WO        2020067591 A1    4/2020

OTHER PUBLICATIONS

PCT International Search Report & Written Opinion dated Sep. 24, 2021 for corresponding PCT International Application PCT/US2021/032469.  
(Continued)

*Primary Examiner* — Jafar F Parsa  
(74) *Attorney, Agent, or Firm* — Domingos J. Silva; Kevin T. O'Brien; SAUL EWING LLP

(57) ABSTRACT

Provided herein are $TiO_{2-x}$ nanoparticles and materials that show unusual photophysical and optical properties. These $TiO_{2-x}$ particles and materials can be used as efficient photocatalysts for the reduction of $CO_2$ with $H_2O$ to produce  
(Continued)

$CH_4$. Also provided herein are methods of making $TiO_{2-x}$ nanoparticles using a polymer-derived mesoporous carbon (PDMC) as a template.

9 Claims, 12 Drawing Sheets

(51) Int. Cl.

| | |
|---|---|
| *B01J 35/45* | (2024.01) |
| *B01J 35/61* | (2024.01) |
| *B01J 35/63* | (2024.01) |
| *B01J 35/64* | (2024.01) |
| *B01J 37/08* | (2006.01) |
| *C01G 23/04* | (2006.01) |
| *C07C 1/12* | (2006.01) |

(52) U.S. Cl.
CPC ........... *B01J 35/615* (2024.01); *B01J 35/633* (2024.01); *B01J 35/647* (2024.01); *B01J 37/086* (2013.01); *C01G 23/043* (2013.01); *C07C 1/12* (2013.01); *C01P 2004/64* (2013.01); *C01P 2006/12* (2013.01); *C01P 2006/14* (2013.01); *C01P 2006/16* (2013.01); *C07C 2521/06* (2013.01)

(56) References Cited

U.S. PATENT DOCUMENTS

| | | | |
|---|---|---|---|
| 2018/0161760 A1 | 6/2018 | Iida et al. | |
| 2018/0311643 A1 | 11/2018 | Okuno et al. | |
| 2018/0318795 A1* | 11/2018 | Yu | B01J 37/34 |
| 2020/0071186 A1 | 3/2020 | Li et al. | |

OTHER PUBLICATIONS

Habisreutinger, Severin N., et al., "Photocatalytic Reduction of CO2 on TiO2 and Other Semiconductors", Angew Chem Int Ed, 52 (29), Jun. 13, 2013, 7372-7851.

Kang, In-Cheol , et al., "Preparation of a visible sensitive carbon doped TiO2 photo-catalyst by grinding TiO2 with ethanol and heating treatment", Applied Catalysis B. Environmental, vol. 80, Apr. 14, 2008, 81-87.

Yaghoubi, Houman et al., "Toward a Visible Light-Driven Photocatalyst: The Effect of Midgap-States-Induced Energy Gap of Undoped TiO2 Nanoparticles", ACS Catalysis, vol. 5, (No. 1, 2), Jan. 2, 2015, 327-335.

EP Search Report, EP Appl. 21 80 4894, Jul. 2, 2024.

* cited by examiner

| curr | HV ↵ | bias | det | mode | mag ⊞ | WD | HFW | ——— 500 nm ——— |
| 0.10 nA | 500.00 V | 2000 V | TLD | BD | 35 000 x | 4.6 mm | 2.84 μm | Magellan ISI Brno |

TITANIUM DIOXIDE PARTICLES AND METHODS OF MAKING THE SAME

CROSS-REFERENCE TO RELATED APPLICATIONS

This application is a 35 U.S.C. § 371 national phase application from, and claims priority to, PCT International Patent Application No. PCT/US2021/032469, filed May 14, 2021, which claims the benefit of priority under 35 U.S.C. § 119(e) to U.S. Provisional Patent Application Ser. No. 63/025,225, entitled "TITANIUM DIOXIDE PARTICLES AND METHODS OF MAKING THE SAME," filed May 15, 2020, the disclosures of which i-s are incorporated herein by reference in their entireties.

STATEMENT REGARDING FEDERALLY SPONSORED RESEARCH

This invention was made with government support under Grant Nos. CBET-1508611 and DMR-1508611 awarded by the National Science Foundation. The government has certain rights in this invention.

BACKGROUND

Nanostructured materials have interesting electronic, optical and magnetic properties, often drastically different from their bulk counterparts. Many of their properties can be further tuned and optimized for specific applications by changing the nanoscale size, shape, and structural/chemical compositions of the materials. This can be achieved, for example, through doping the nanomaterials with other elements (metals and heteroatoms), by conjugating them with other materials and creating heterojunctions, and by introducing nanopores into their surfaces.

With the global production of over 10 million metric tons, $TiO_2$ is one of the most widely used materials for various applications. Examples of its applications include commercial sunscreens, self-cleaning, paints, cosmetic products, and varnishes. $TiO_2$ is also used in the paper/pulp, plastic, fiber, rubber, food, glass and ceramic industries. In nanosized powder forms, $TiO_2$ has been explored for various photocatalytic reactions including water splitting and $CO_2$ reduction. $TiO_2$ is attractive for all these applications because of its semiconducting properties, inexpensiveness, environmental friendliness, and stability under various conditions. However, $TiO_2$ is not very efficient in driving photocatalytic reactions for the following two reasons: (a) $TiO_2$ has a large band gap (3.2 eV) and is thus capable of absorbing light only in the UV region of solar spectrum (ca. 3% of total solar spectrum), and (b) photoexcited electrons and holes in pristine $TiO_2$ have fast recombination times, resulting in poor performance in redox reactions.

While photocatalysis research on $TiO_2$ has a long history, $TiO_2$-based photocatalysis aimed to green energy applications has recently received renewed interest. One prominent example is utilizing $TiO_2$ photocatalysts in the hydrogen evolution reaction (HER) to produce hydrogen ($H_2$), a clean energy carrier, from water. Another example is converting the greenhouse gas $CO_2$, which is largely produced from the combustion of fossil fuels and which continues to pose a danger of global warming, into synthetic fuels and valuable chemical feedstocks (such as $CH_4$, $CH_3OH$, HCOOH, carbonates and carbamates). Although photochemical reduction of $CO_2$, using water or $H_2$, have long been demonstrated, the problem still remains on improving a quantum efficiency (i.e., the proportion of light quanta utilized in a catalytic reaction out of total number of quanta absorbed) in the reaction. Large scale applications are still awaiting for availability of large-surface-area and sustainable $TiO_2$ catalysts, specifically engineered for efficient reduction of $CO_2$. In particular, catalysts that can do so with sustainable energy sources such as sunlight are of paramount importance to scale-up the process for a broad range of applications.

Demands for novel materials that can be used for photochemical transformations with improved quantum efficiency are still high. The present invention addresses and meets this need.

BRIEF SUMMARY OF THE INVENTION

In various aspects, a material titanium oxide material containing $TiO_{2-x}$ is provided. The material has a light absorption onset of about 400 nm to about 510 nm, and x is a number ranging from 0.001 to 0.100. In various aspects, a method of making a titanium oxide particle is provided. The method includes contacting a titanium-containing compound with at least one polymer-derived mesoporous carbon (PDMC) material; and heating the titanium-containing compound and the PDMC at a temperature of about 500 to 1200° C. in an inert atmosphere to form titanium oxide particles. Advantageously, in various aspects, the titanium oxide materials described herein can reduce carbon dioxide as provided in the method described herein. The method includes contacting a gas comprising $CO_2$ with any of the titanium oxide materials described herein in the presence of light; and reducing the $CO_2$ to provide $CH_4$.

BRIEF DESCRIPTION OF THE FIGURES

The drawings illustrate generally, by way of example, but not by way of limitation, various embodiments of the present application.

(FIGS. 2A, 2B) Low voltage (LV) SEM images of PDMC obtained with 0.5 keV electron beam. LV STEM images of (FIG. 2C) $TiO_{2-x}$/PDMC and (FIG. 2D) $TiO_{2-x}$ materials obtained with 10 keV electron beam. TEM images of single particles of (FIG. 2E) TGM, (FIG. 2F) $TiO_2$—(C), (FIG. 2G) $TiO_2$—(H), (FIG. 2H) $TiO_2$—(H+C) and (FIG. 2I) $TiO_{2-x}$.

(FIG. 3A) Thermogravimetric analysis (TGA) curves obtained in air atmosphere for PDMC and $TiO_{2-x}$/PDMC materials by raising the temperature and holding it at 550° C. for 30 min. (FIG. 3B) Physical appearance of $TiO_{2-x}$ and $TiO_2$—(H+C) and (FIG. 3C) UV-visible diffuse reflectance spectra of $TiO_2$—(H+C) and $TiO_{2-x}$ materials. (FIG. 3D) XRD patterns of $TiO_2$—(H+C)

and $TiO_{2-x}$. (FIG. 3E) $N_2$ adsorption/desorption isotherms of PDMC and $TiO_2$-x/PDMC and (FIG. 3F) their corresponding pore size distributions. (FIG. 3G) $N_2$ adsorption/desorption isotherms of $TiO_2$—(H+C) and $TiO_{2-x}$ and (FIG. 3H) their corresponding pore size distributions.

(FIG. 4C) Broad field-range EPR spectra of $TiO_{2-x}$ after UV irradiation, measured at two temperatures: 20 K (blue trace) and 50 K (red trace). The broad baseline signal spanning from 100 to 1100 mT is due to weakly-localized electrons/holes and their conductive coupling to electric microwave field through charge hopping and cyclotron motion.

(FIG. 5A, 5B) LV SEM images of $TiO_{2-x}$/PDMC taken while the $TiO_{2-x}$ nanoparticles lighting up and fading away under a beam of slow energy electrons in the dark field detector segment (to highlight the material contrast) at 10 keV. The bright spots marked with red arrows are the $TiO_{2-x}$ particles that show the blinking behavior. (FIG. 5C) Time evolution of brightness intensity for one of the $TiO_{2-x}$ nanoparticles taken under the electron beam at 30 keV. The brightness intensity changes between two discrete levels (ON and OFF), indicating that charging/discharging by only one electron is probably involved. The average switching time between ON/OFF states is ca. 15 s.

DETAILED DESCRIPTION OF THE INVENTION

Figure 1:
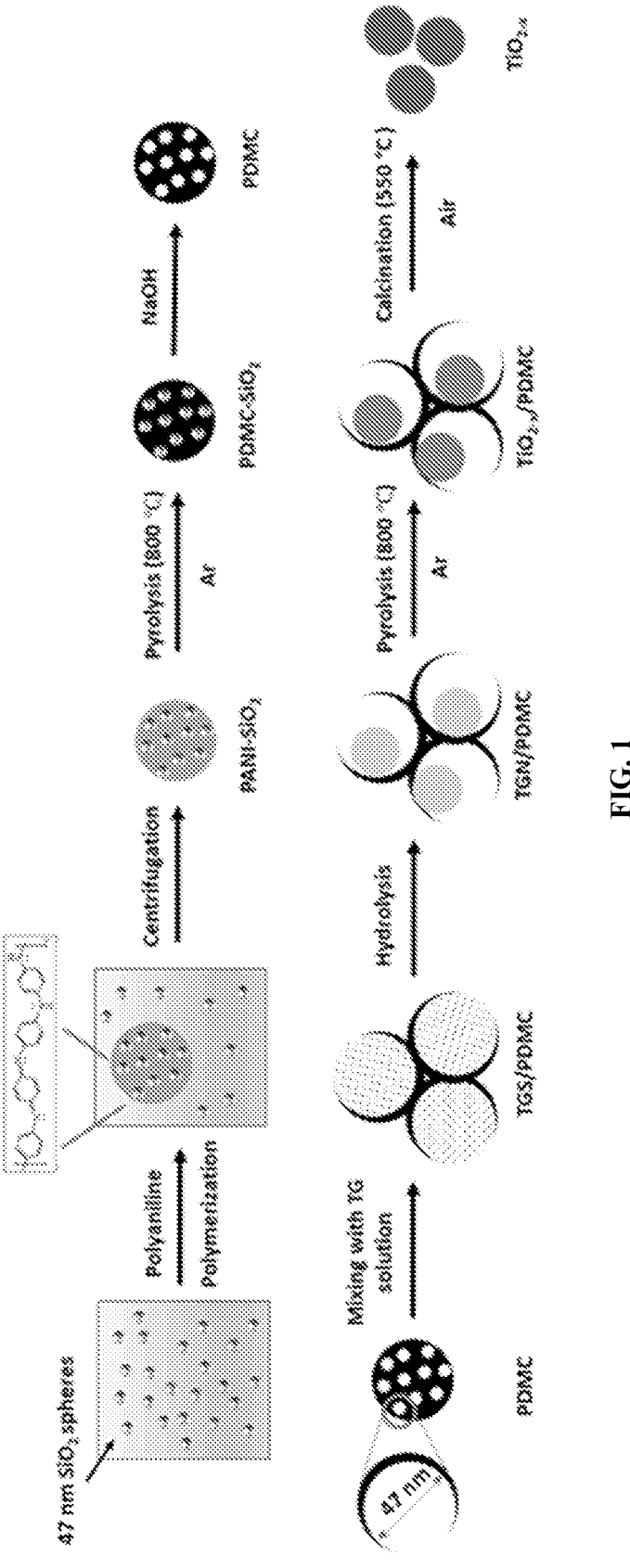
FIG. 1 illustrates a schematic illustration of one embodiment of the procedure to synthesize $TiO_{2-x}$/PDMC and $TiO_{2-x}$. First, PANI (polyaniline)-derived mesoporous carbon (PDMC) is prepared by polymerizing PANI with colloidal silica ($SiO_2$), then pyrolyzing the PANI/$SiO_2$ under Ar atmosphere, and finally etching away $SiO_2$. The resulting material, PDMC, is used as a template for the synthesis of $TiO_{2-x}$/PDMC. To do so, titanium glycolate (TG) solution is infiltrated into the mesopores of PDMC to form TG nanoparticles-loaded PDMC (TGN/PDMC). After pyrolysis of TGN/PDMC, $TiO_{2-x}$/PDMC is formed. When the PDMC template is removed by calcination, mesoporous $TiO_{2-x}$ is produced.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

As used herein, the term "electromagnetic radiation" includes radiation of one or more frequencies encompassed within the electromagnetic spectrum. Non-limiting examples of electromagnetic radiation comprise gamma radiation, X-ray radiation, UV radiation, visible radiation, infrared radiation, microwave radiation, radio waves, and electron beam (e-beam) radiation. In one aspect, electromagnetic radiation comprises ultraviolet radiation (wavelength from about 10 nm to about 400 nm), visible radiation (wavelength from about 400 nm to about 750 nm) or infrared radiation (radiation wavelength from about 750 nm to about 300,000 nm). Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In one embodiment, the UV light source emits light between about 350 nm and about 400 nm. In some embodiments, the UV light source emits light between about 400 nm and about 500 nm.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "solvent" as used herein refers to a liquid that can dissolve a solid, liquid, and/or gas. Non-limiting examples of solvents are silicones, organic compounds, water, alcohols, ionic liquids, and/or supercritical fluids.

The term "independently selected from" as used herein refers to referenced groups being the same, different, or a mixture thereof, unless the context clearly indicates otherwise.

Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "standard temperature and pressure" as used herein refers to 20° C. and 101 kPa.

Titanium Dioxide Particles and Materials

In certain embodiments, a particle of $TiO_{2-x}$ or a plurality of $TiO_{2-x}$ particles is/are provided. In various embodiments, the $TiO_{2-x}$ particle is a $TiO_{2-x}$ nanoparticle. The plurality of $TiO_{2-x}$ particles can neck or adhere together and form a porous $TiO_{2-x}$ material. The porous $TiO_{2-x}$ material can have a light absorption onset of about 400 nm to about 510 nm, and x is a number ranging from about 0.001 to about 0.100.

The light absorption onset of the porous $TiO_{2-x}$ material can be, in certain embodiments, about 400, 405, 401, 415, 420, 425, 430, 435, 440, 445, 450, 455, 460, 465, 470, 475, 480, 482, 484, 486, 488, 490, 492, 494, 496, 498, 500, 502, 504, 506, 508, or about 510 nm. In certain embodiments, the $TiO_{2-x}$ particle is in an anatase phase. The $TiO_{2-x}$ particle or particles can be, in certain embodiments, at least about 90, 91, 92, 93, 94, 95, 96, 97, 98, 99, 99.5, 99.9, or 99.99% in the anatase phase. The portion of the particle not in the anatase phase is, in certain embodiments, in the rutile phase. The $TiO_{2-x}$ particle can also be 100% anatase phase.

The value of 'x' can be, in certain embodiments, about 0.001, 0.005, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, or 0.100. In certain embodiments, a plurality of $TiO_{2-x}$ particles does not substantially aggregate. In certain embodiments, the $TiO_{2-x}$ particles described herein do not adhere to each other and form agglomerates of particles, for example. In certain embodiments, the $TiO_{2-x}$ particles described herein remain stable under ambient condition for several days, for example. In certain embodiments, the $TiO_{2-x}$ particles described herein have slightly yellowish color and keep this color for several days, for example. In certain embodiments, the $TiO_{2-x}$ particles described herein remain stable high temperature up to 1200° C., for example.

In certain embodiments, the $TiO_{2-x}$ nanoparticle can have an average size of about 1 to about 20 nm, or about 5 to about 12 nm. The average size of the $TiO_{2-x}$ nanoparticle can be, in one embodiment, about 1, 1.5, 2, 2.5, 3, 3.5, 4, 4.5, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 11.2, 11.4, 11.6, 11.8, 12, 13, 14, 15, 16, 17, 18, 19, or about 20 nm. The average size of the $TiO_{2-x}$ nanoparticle can be determined by measuring the particle diameter or the largest linear dimension of the nanoparticle.

The $TiO_{2-x}$ porous material can, in some embodiments, have a pore size of about 2 nm to about 60 nm, or about 5 nm to about 30 nm, or about 5 nm to about 15 nm. In one embodiment, the pore size of the $TiO_{2-x}$ porous material can be about 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or about 60 nm.

In certain embodiments, the $TiO_{2-x}$ porous material can have a BET surface area of about 30 to about 210 m$^2$ g$^{-1}$, about 50 to about 160 m$^2$ g$^{-1}$, or about 70 to about 110 m$^2$ g$^{-1}$. The BET surface area of the $TiO_{2-x}$ porous material can be, in certain embodiments, about 30, 35, 40, 45, 50, 55, 60, 65, 70, 72, 74, 76, 78, 80, 82, 84, 86, 88, 90, 92, 94, 96, 98, 100, 102, 104, 106, 108, 110, 120, 130, 140, 150, 160, 170, 180, 190, 200, or 210 m$^2$ g$^{-1}$.

In certain embodiments, the $TiO_{2-x}$ porous material can have a pore volume of about 0.1 to about 1 cm$^3$ g$^{-1}$, about 0.1 to about 0.5 cm$^3$ g$^{-1}$, about 0.1 to about 0.3 cm$^3$ g$^{-1}$. In certain embodiments, the $TiO_{2-x}$ porous material can have a pore volume of about 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, or about 1 cm$^3$ g$^{-1}$.

In certain embodiments, the $TiO_{2-x}$ porous material or $TiO_{2-x}$ particle can have at least one of optically-active mid-gap states related to oxygen vacancies or interstitial $Ti^{3+}$ species. In one embodiment, the interstitial $Ti^{3+}$ species can include a plurality of under-coordinated O$^-$ groups. In some embodiments, the titanium dioxide particles or materials described herein do not contain any other substance that affects the properties described herein.

Methods of Making Titanium Dioxide Particles and Titanium Dioxide Porous Materials In certain embodiments, methods of making a titanium oxide particle or porous material are provided. In certain embodiments, the method includes contacting a titanium-containing compound with at least one polymer-derived mesoporous carbon (PDMC) material and heating the titanium-containing compound and the PDMC in an inert atmosphere at a temperature of about 500 to 1200° C. to form titanium oxide particles. The inert atmosphere can be any suitable non-oxygen containing gas, such as nitrogen, argon, and the like. Suitable titanium-containing compounds can include titanium tetrachloride, titanium tetrabutoxide, titanium tetraisopropanolate, titanium glycolate, and the like. In a certain embodiment, the titanium-containing compound is titanium glycolate. PDMC materials can be made using suitable carbon sources, including polyaniline, polypyrrole, thermosetting phenol resin, mesophase pitch, polyacrylonitrile, and the like. PDMC's can be made using appropriately sized silica ($SiO_2$) particles as templates according to methods known in the art and as described herein. In certain embodiments, the PDMC material can include polymerized aniline (PANI).

The PDMC material, in various embodiments, can have an average pore size of about 2 nm to about 120 nm, about 20 nm to about 90 nm, or about 40 nm to about 70 nm. The PDMC material can have an average pore size, in some embodiments, of about 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, or 120 nm.

In certain embodiments, the heating step includes forming $TiO_{2-x}$ nanoparticles with any of the properties or dimensions described herein. The heating step can be performed at a temperature of about 500, 550, 600, 650, 700, 750, 800, 850, 900, 950, 1000, 1050, 1100, 1150, or 1200° C. The method can further include calcining the $TiO_{2-x}$ nanoparticles and the PDMC in air. The calcining step, in certain embodiments, removes the PDMC material (by pyrolysis), leaving only the titanium oxide material. In certain embodiments, the calcining removes the PDCM and provides $TiO_{2-x}$ porous material. In certain embodiments, the calcining step is at a temperature of about 450 to 750° C., or about 450, 475, 500, 525, 550, 575, 600, 625, 650, 675, 700, 725, and 750° C.

Calcination of the PDMC material containing $TiO_{2-x}$ nanoparticles can result in necking of the $TiO_{2-x}$ nanoparticles to form a $TiO_{2-x}$ porous material. Without being bound by theory, it is believed that infiltration of the pores in the PDMC material with the titanium-containing compound or a solution of the titanium-containing compound during the heating step results in formation of the $TiO_{2-x}$ nanoparticles.

In certain embodiments, the titanium oxide material produced by the method described herein can have an average pore size of about 5 to about 12 nm, a BET surface area of about 70 to about 110 $m^2$ $g^{-1}$, a pore volume of about 0.1 to about 0.3 $cm^3$ $g^{-1}$, or a combination thereof. In certain embodiments, the titanium oxide particle has a light absorption onset of about 400 nm to about 510 nm.

Methods of Photocatalytic $CO_2$ Reduction

In certain embodiments, method of reducing carbon dioxide are provided. In certain embodiments, the method includes contacting a gas containing $CO_2$ with any of the titanium dioxide particles or materials described herein in the presence of light and reducing the $CO_2$ to provide $CH_4$. Surprisingly, the titanium dioxide materials described herein can produce $CH_4$ at a rate of at least about, greater than, or about 16, 17, 18, 19, 20, 21, 22, 23, 24, 25, 26, 27, 28, 29, 30, 31, 32, 33, 34, or 35 $\mu mol$ $h^{-1}$ $g^{-1}$. The gas containing $CO_2$ can be any suitable gas containing some amount of $CO_2$, including combustion exhaust, the atmosphere, individual exhalation, and the like. In certain embodiments, the light can be ultraviolet radiation. The particles or porous materials described herein may be suitably adsorbed by or adhered to a solid support and used in photocatalytic applications.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions with art-recognized alternatives and using no more than routine experimentation, are within the scope of the present application.

It should be understood that the method and compositions that would be useful in the present invention are not limited to the particular formulations set forth in the examples. The following examples are put forth so as to provide those of ordinary skill in the art with a complete disclosure and description of how to make and use the composition and therapeutic methods of the invention, and are not intended to limit the scope of what the inventor regard as his invention.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples, therefore, specifically point out selected embodiments of the present invention, and are not to be construed as limiting in any way the remainder of the disclosure.

Chemicals and Reagents. Aniline (≥99.5%), ammonium persulfate (≥98.0%), sodium hydroxide (≥97.0%), hydrochloric acid (37%), titanium(IV) n-butoxide (97%), ethylene glycol (anhydrous, 99.8%), ammonium persulfate (≥98.0%) and acetone (HPLC Plus grade, >99.9%) were purchased from Sigma-Aldrich. Colloidal silica (SNOWTEX©) with nominal particle size of 47 nm was obtained from Nissan Chemical America Corporation. Anhydrous ethanol was obtained from Fisher Scientific. The chemicals and reagents were all used as received. Distilled water was used for the experiments.

Synthesis of Polyaniline (PANI)-derived Mesoporous Carbon (PDMC). A composite material composed of PANI and silica nanoparticles was synthesized by polymerizing aniline, initiated by ammonium persulfate, in the presence of colloidal silica templates. Typically, colloidal silica (30 g) was mixed with aqueous HCl solution (1 M, 120 mL) containing aniline (2 mL). The solution was stirred for 30 min in a water bath whose temperature was maintained in between 0 and 5° C. Then, into the solution under stirring, aqueous HCl solution (1 M, 20 mL) containing ammonium persulfate (5 g) was added drop-wise. The solution was further stirred for 24 h between 0 and 5° C., and then kept in oven at 100° C. to let the solvent evaporate. The resulting green-colored solid material, PANI/silica, was pyrolyzed under Ar atmosphere at 800° C. for 2 h, after raising the temperature from room temperature to 800° C. at a rate of 5° C. $min^{-1}$. The black powdered product (800 mg) was subsequently treated with aqueous NaOH solution (2 M, 54 mL) in an autoclave at 100° C. for 24 h to remove the silica templates. Finally, the mixture was filtered, and the solid product was washed with water (80 mL, 4 times) and EtOH (20 mL, 2 times), and then dried at 50° C. This produced PDMC.

PDMC-Assisted Synthesis of $TiO_{2-x}$ Material. First, titanium(IV) n-butoxide (1 mL) and ethylene glycol (20 mL) were mixed and stirred together for 4 h to form titanium glycolate (TG) solution. Then, using a MilliporeSigma Glass Vacuum Filter Assembly, in which a Pall Universal Membrane Disc Filter (0.45 μm, 25 mm) containing PDMC (300 mg) was placed, the TG solution was slowly poured while being pumped through with a vacuum pump to infiltrate the TG into the pores of PDMC. The TG solution loaded PDMC was dispersed in a solution of acetone (20 mL) and water (320 μL), and the mixture was stirred for 12 h, which led to the formation of TG nanoparticles (TGN) in the pores of PDMC. The solid material was collected via centrifugation and dried at 60° C. The resulting material, TGN/PDMC, was placed on a ceramic combustion boat in a temperature-programmable tube furnace and pyrolyzed under Ar atmosphere as follows. The temperature was first raised from room temperature to 800° C. at a rate of 5° C. $min^{-1}$ and kept at 800° C. for 2 h. The furnace was then let to cool down to room temperature naturally. After pyrolysis, TGN/PDMC became $TiO_{2-x}$/PDMC. The PDMC template in $TiO_{2-x}$/PDMC was removed by calcining the material at 550° C. in air for 30 min. This gave mesoporous $TiO_{2-x}$.

Synthesis of Control $TiO_2$ Materials via Calcination or Hydrolysis+Calcination.

For comparative studies, two control $TiO_2$ materials were synthesized as follows. First, titanium(IV) n-butoxide (2 mL) and ethylene glycol (50 mL) were mixed and stirred together for 4 h to produce a colloidal solution of TG microspheres (TGMs). This solution was then poured into another solution containing acetone (170 mL) and water (2 mL). After stirring for 1 h, the solution was centrifuged. The precipitate was washed with ethanol (via stirring, centrifugation and decantation) and dried at 60° C. The resulting white solid material, which contained TGMs, was then calcined in air at 800° C. for 2 h, after raising the temperature from room temperature to 800° C. at a rate of 5° C. $min^{-1}$. This gave a $TiO_2$ material that is denoted as $TiO_2$—(C), where "C" represents "a material synthesized by calcination".

In another experiment, the TGMs were refluxed in a boiling water for 24 h. The mixture was centrifuged, and the precipitate was then washed with ethanol (via stirring, centrifugation and decantation) and dried at 60° C. The resulting material, dubbed $TiO_2$—(H), where "H" represents "a material synthesized by hydrolysis", was then calcined at 500° C. This gave a $TiO_2$ material that is named $TiO_2$—(H+C).

Characterizations. Transmission electron microscope (TEM) images of the materials were taken with a Topcon 002B TEM instrument operating at 200 kV. Low energy electron beam S(T)EM images were obtained using a Magellan 400 microscope (FEI) that was operating in a beam deceleration mode. The microscope was equipped with a home-designed sample holder suitable for scanning low energy electron microscopy (SLEEM). The beam deceleration was achieved with a relatively simple method by applying a negative bias on the sample holder. This was done in order to improve both the resolution and the contrast of the images. The instrument was operated by adjusting the electron energy in the range of ca. 0 eV to 30 keV until a good image was obtained. While using an electron beam with energy of 500 eV (or 0.5 keV) in a reflection mode and 10 keV in a transmission mode, the $TiO_{2-x}$ nanoparticles continuously brightened up and faded away every ca. 15 s, due to charging and discharging.

The surface areas and pore properties of the materials were investigated by $N_2$ porosimetry using a Tristar-3000 instrument (Micromeritics, USA). Before each measurement, the sample was degassed at 80° C. for 8 h under a flow of dry $N_2$ gas to remove any possible guest species adsorbed on the samples' surfaces. The surface areas and pore size distributions of the materials were calculated using the Brunauer-Emmett-Teller (BET) method and the Barrett-Joyner-Halenda (BJH) method, respectively. The pore volumes of the materials were determined based on the amount of $N_2$ adsorbed at a relative pressure of 0.99.

X-ray diffraction (XRD) patterns of the materials were obtained using a Philips X'Pert diffractometer operating with Cu Kα X-ray source. The XRD diffraction patterns were recorded in a 2θ range between 10° and 80° with a step size (2θ) of 0.02° and a scan rate of 0.6° $min^{-1}$. The UV-Vis diffuse reflectance spectra (UV-Vis DRS) of the materials were acquired with a Lambda 950 spectrophotometer (PerkinElmer) in a spectral range of 250 nm to 800 nm. Thermogravimetric analyses (TGA) of the materials were carried out using a PerkinElmer TGA7 instrument by heating the samples at a rate of 5° C. $min^{-1}$ under a flow of air at a rate of 20 mL $min^{-1}$. Elemental compositions of the materials were analyzed with a K-Alpha X-ray photoemission spectrometer (XPS) equipped with Al Kα X-ray source (hv=1486.6 eV) (Thermo Scientific).

Electron paramagnetic resonance (EPR) experiments were performed using an Elexsys E580e spectrometer (Bruker) that was operating at X-band (9.5 GHz) and utilizing a standard $TE_{102}$ resonator with an ESR900 flow cryostat (Oxford Instruments). To prepare the EPR samples, the weighted quantities of $TiO_{2-x}$ and $TiO_2$—(H+C) powders were placed in quartz EPR tubes (OD 4 mm) and then flame sealed under atmospheric air. The samples were irradiated with UV light in a separate finger Dewar at liquid nitrogen temperature (77 K) using a 4 W split-tube lamp (UVGL-15, 254/365 nm). The UV exposure time was about 25-30 min, and the samples were periodically rotated to allow more uniform light exposure. The density of EPR-visible defects in each sample was determined by comparing the measured EPR signal intensities to the EPR standard with a known number of spins (a $CuSO_4 \cdot 5H_2O$ crystal of known weight in mineral oil).

Physical characterization of synthesized materials. In the first step (FIG. 1), aniline is polymerized in the presence of colloidal silica templates using ammonium persulfate as an oxidant. The resulting PANI-$SiO_2$ composite material is treated at 800° C. for 2 h under Ar atmosphere to pyrolyze PANI. When the $SiO_2$ templates are subsequently etched away with an aqueous alkaline solution, PDMC is formed. Into the mesopores of the PDMC, TG solution is infiltrated, and the resulting TGN/PDMC is then pyrolyzed at 800° C. This generates $TiO_{2-x}$/PDMC. When the PDMC template is calcined at 550° C. in air for 30 min, the PDMC is removed and a mesoporous $TiO_{2-x}$ material is obtained.

Figures 2A, 2B, 2C, 2D, 2E, 2F, 2G, 2H, 2I:
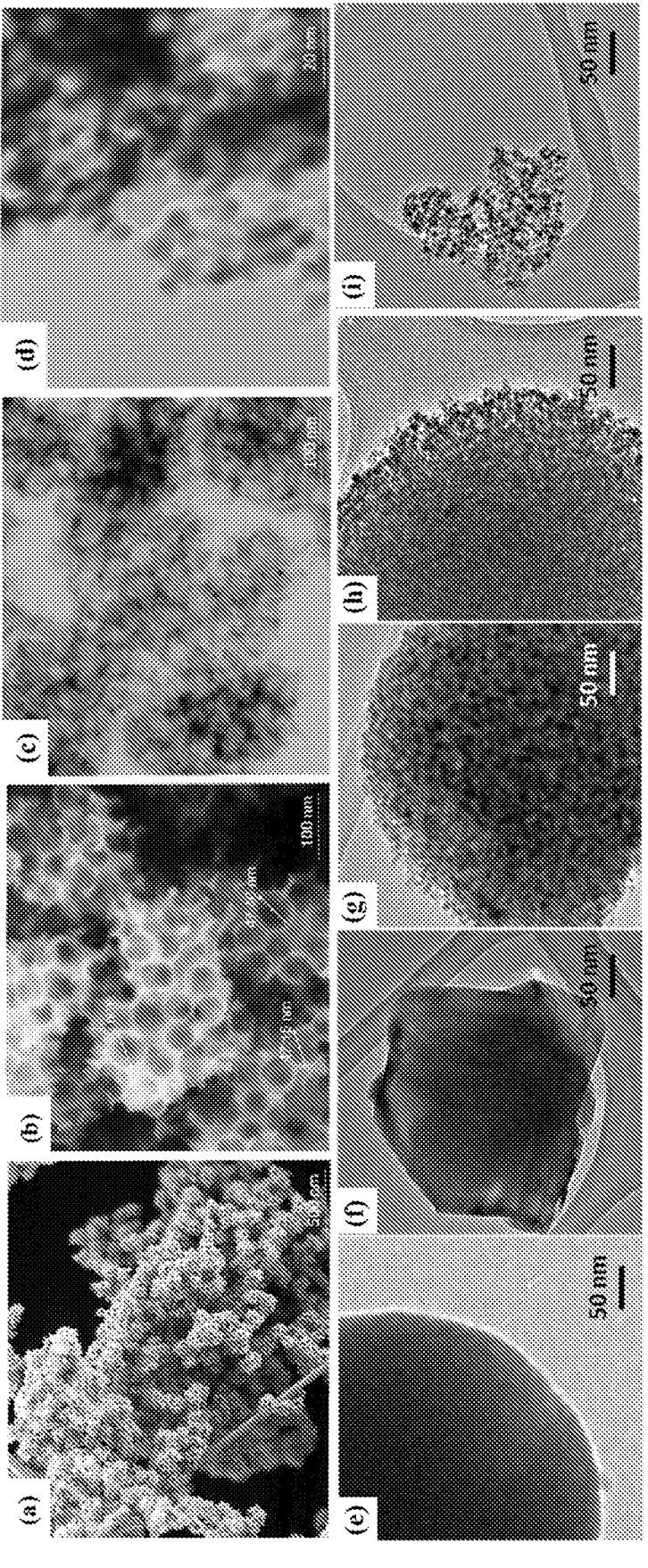
FIGS. 2A-2I illustrate high-resolution S(T)EM (scanning (transmission) electron microscopy) imaging of the synthesized $TiO_2$ materials.

The morphologies of PDMC, $TiO_{2-x}$/PDMC and $TiO_{2-x}$ are examined by low-voltage SEM/STEM (FIG. 2). The images of PDMC reveal that the material possesses highly mesoporous structures with an average pore size of ca. 47 nm (FIGS. 2A and 2B). The images of $TiO_{2-x}$/PDMC show nanoparticles with an average size of ca. 8 nm inside the pores of PDMC (FIG. 2C). The nanoparticles, which are found to be $TiO_{2-x}$ nanoparticles (see below), maintain their shape and size, without much aggregation, even after the removal of PDMC template by calcination at 550° C. (see FIGS. 2D and 2I). The regular STEM and SEM images of the materials obtained using high voltage, displayed in FIGS. 7A-7F, 8, and 9, also show similar structures but appear slightly blurred compared with those obtained using a low voltage.

For comparison, the structures of single particles of TGM, $TiO_2$—(C), $TiO_2$—(H), $TiO_2$—(H+C) and $TiO_{2-x}$ are imaged by a TEM (FIGS. 2E-2I). The image of a single TGM microparticle shows spherical shape (FIG. 2E) whereas that of $TiO_2$—(C) particle, which is derived from a TGM microparticle by calcination, shows slightly deformed shape (FIG. 2F). This deformation from spherical shape is seen in all of the particles of $TiO_2$—(C). Meanwhile, $TiO_2$—(H), which is prepared by hydrolyzing TGM in a boiling water, shows nanoporous structures composed of closely packed nanosized grains of ca. 6-9 nm in size (FIG. 2G). After treatment at 500° C. for 2 h, and becoming $TiO_2$—(H+C), the microparticle shows more nanoporous structure that is composed of nanoparticles with an average size of ca. 8 nm (FIG. 2H). The microparticle maintains the original spherical morphology after calcination (this is unlike that of $TiO_2$—(C), which undergoes deformation after the thermal treatment, see the image in FIG. 2F). The image for $TiO_{2-x}$ shows nanoporous structure (FIG. 2I).

Figures 3A, 3B, 3C, 3D, 3E, 3F, 3G, 3H:
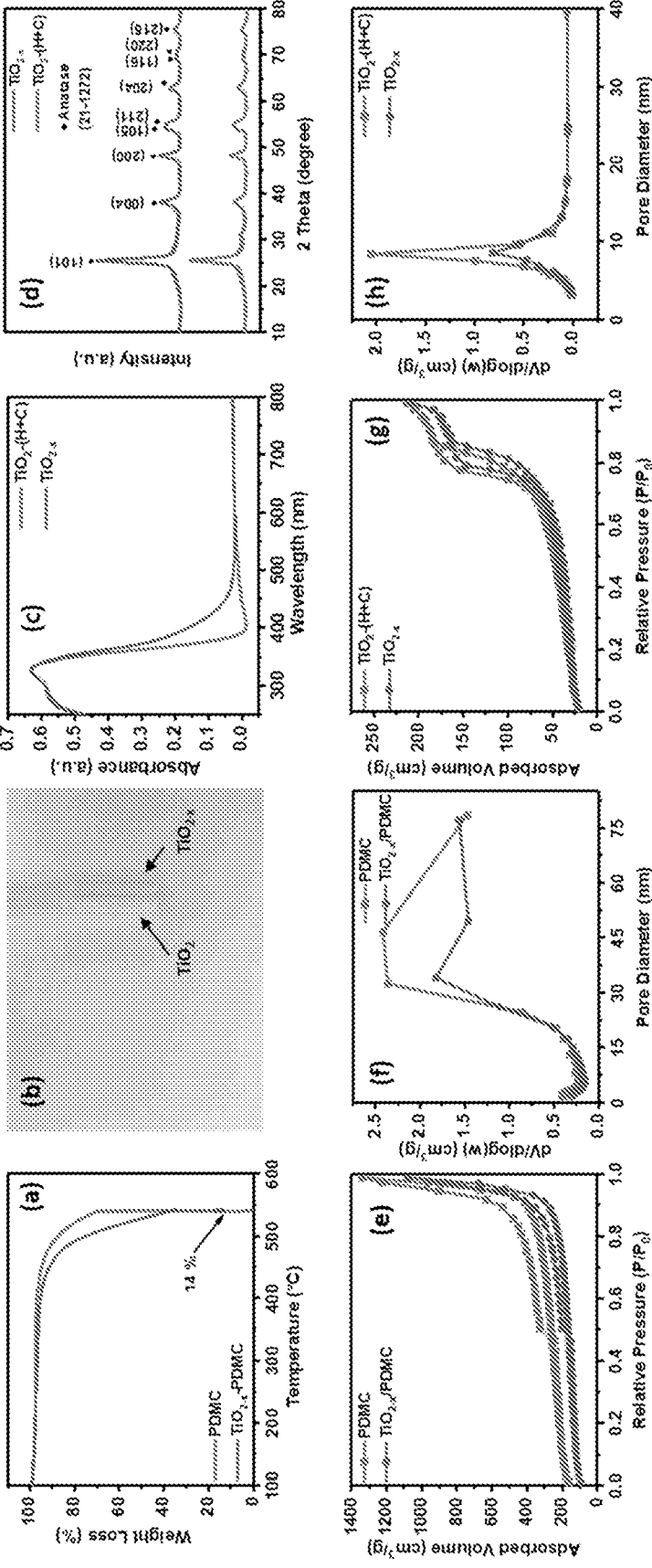
FIGS. 3A-3H illustrate the physical characterization of the $TiO_2$ materials.
Figure 10:
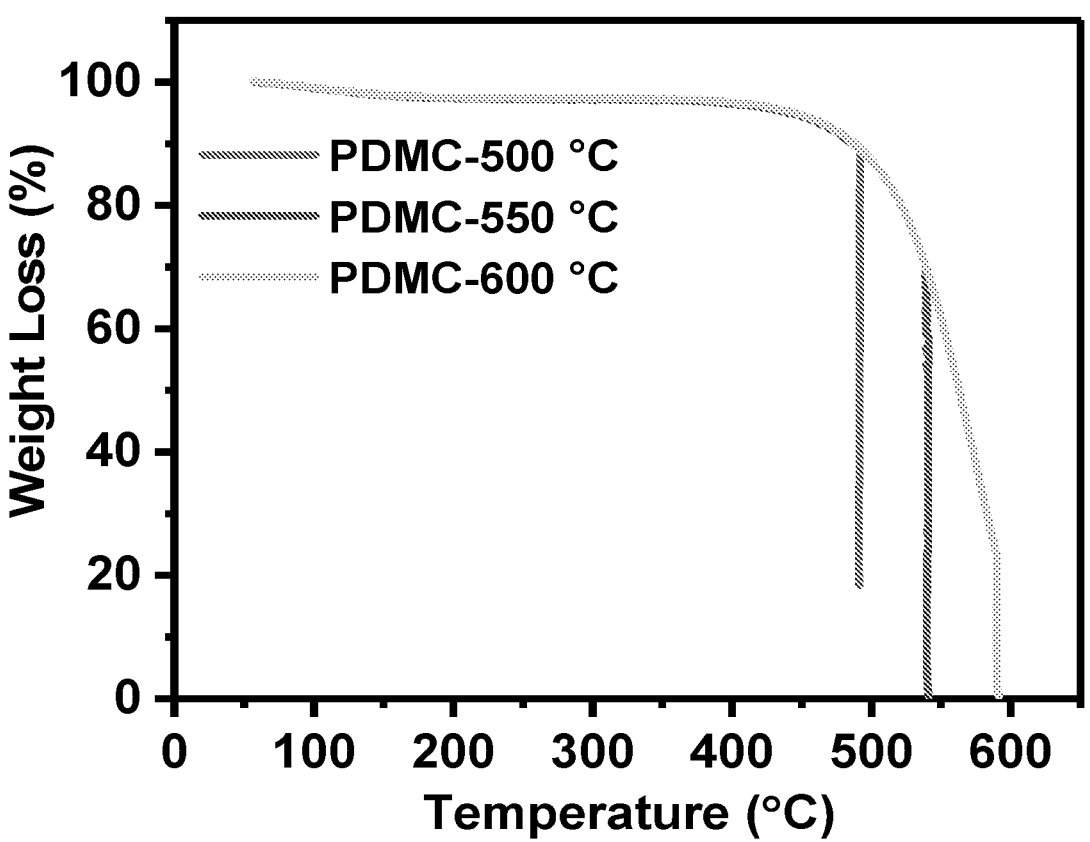
FIG. 10 illustrates thermogravimetric analysis (TGA) curves for PDMC obtained by calcining the sample in air from room temperature to 500, 550 or 600° C., and then holding the temperature at 500, 550 or 600° C. for 30 min.
Figure 11:
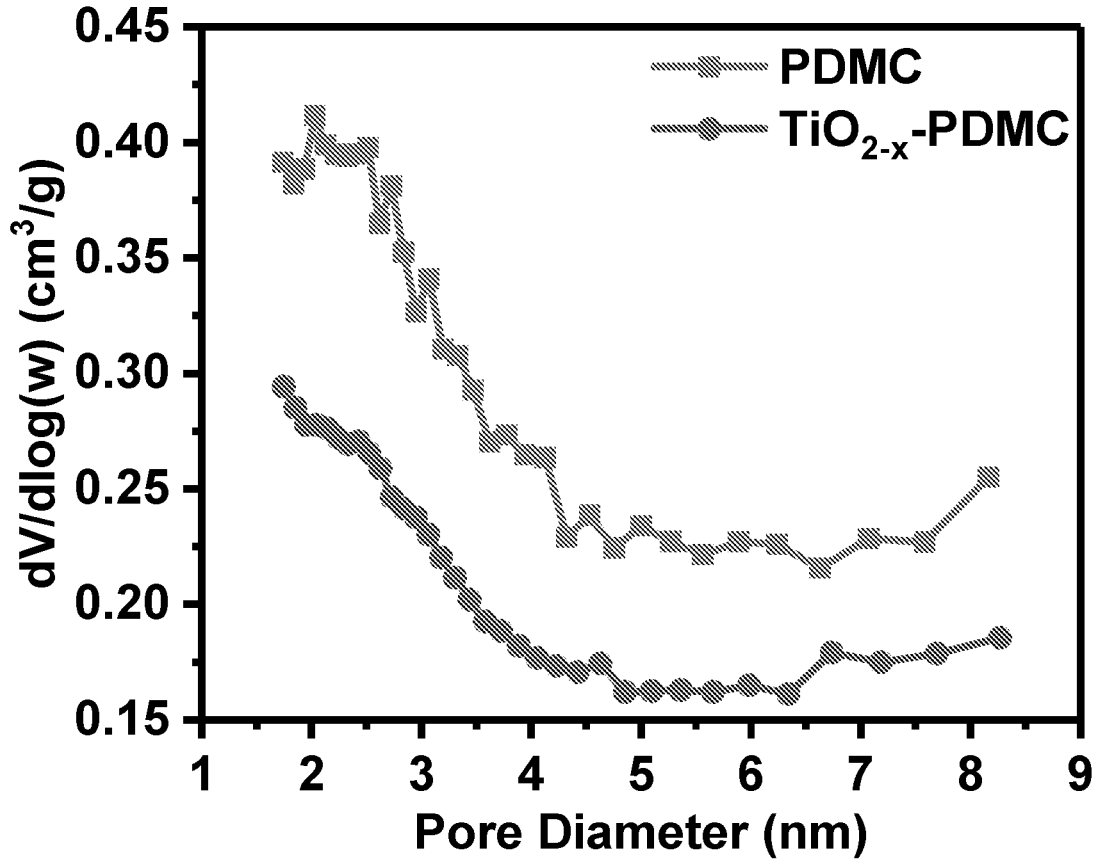
FIG. 11 illustrates pore size distribution of PDMC and $TiO_{2-x}$/PDMC in the range of 1.5 to 8.5 nm. These results show the presence of micropores and small mesopores in the materials. The full pore size distributions of both materials are depicted in FIGS. 4A-4C.

Thermogravimetric analysis (TGA) is carried out under air, first to determine the temperature required to remove the PDMC template from $TiO_{2-x}$/PDMC as well as to estimate the amount of $TiO_{2-x}$ loaded in the PDMC (see FIGS. 3A and 10). The TGA curves are obtained by heating the samples from room temperature to 500, 550 or 600° C. at a rate of 5° C. $min^{-1}$ and then keeping them at the respective maximum temperature for 30 min. The results reveal that the PDMC cannot be fully removed by holding the temperature at 500° C. for 30 min but that it can be completely removed by keeping it at 550 or 600° C. for 30 min (FIG. 10). The curves showing ca. 100% weight loss in the latter two cases indicate that PDMC as well as $TiO_{2-x}$/PDMC does not contain any leftover $SiO_2$. This suggests that the $SiO_2$ nanoparticles are completely removed after the PDMC/$SiO_2$ is etched with an alkaline solution and before the titania is loaded. Based on the results, a calcination temperature 550° C. and a calcination time of 30 min are chosen to remove the PDMC from $TiO_{2-x}$/PDMC to produce $TiO_{2-x}$.

The amount of $TiO_{2-x}$ in the PDMC is determined by comparing the TGA curve obtained for $TiO_{2-x}$/PDMC in air with that of PDMC (FIG. 3A). A total residual weight of ca. 14% after calcination of $TiO_{2-x}$/PDMC at 550° C. for 30 min is observed, and this weight can be exclusively attributed to $TiO_{2-x}$. It is also worth noting that the decomposition of $TiO_{2-x}$/PDMC starts at ca. 430° C., which is ca. 30° C. lower than that of PDMC. This indicates that the presence of $TiO_{2-x}$ helps the thermal decomposition of PDMC, perhaps by facilitating the heat transfer. The results also indirectly corroborate that titania is successfully loaded in $TiO_{2-x}$/PDMC.

The photos of $TiO_{2-x}$ and $TiO_2$—(H+C) and their UV/Vis diffuse reflectance spectra are provided in FIGS. 3B and 3C. While $TiO_2$—(H+C) has a white color, $TiO_{2-x}$ has a yellowish color. This indicates that the two materials have different light-absorption properties. The yellowish color of $TiO_{2-x}$ also indicates that this material is responsive to visible light unlike most traditional $TiO_2$ materials, which are photoresponsive only to UV light. This visible light absorption character of $TiO_{2-x}$ is further confirmed from its diffuse reflectance spectrum (FIG. 3C). While the absorption edge of $TiO_2$—(H+C) shows up at ca. 390 nm (in the UV region), the one for $TiO_{2-x}$ is red-shifted with the onset value appearing at ca. 500 nm; this implies the presence of optically-active mid-gap states related to oxygen vacancies, interstitial $Ti^{3+}$ species, and undercoordinated $O^-$ groups in the latter. This also means $TiO_{2-x}$ has a better ability to absorb visible light than $TiO_2$—(H+C).

X-ray diffraction (XRD) is used to characterize the crystalline phase and crystallite sizes of the materials. Treatment of TGM or $TiO_2$—(H) at 800° C. leads to the phase transformation from anatase to rutile, accompanied by the growth in sizes of the $TiO_2$ nanocrystals. In marked contrast, the present studies show that both $TiO_{2-x}$ and $TiO_2$—(H+C) preserve their anatase phase and show no evidence of a rutile phase (FIG. 3D). The crystallite sizes in both materials are estimated based on the strongest anatase (101) peak using the Scherrer equation ($d = 0.89\lambda/\beta \cos\theta$), where d, $\lambda$, $\beta$ and $\theta$ are the crystallite size, the wavelength of the X-ray radiation, the full width at half-maximum of the peak in radian and the diffraction angle, respectively). Accordingly, the average crystallite size of $TiO_{2-x}$ and $TiO_2$—(H+C) are found to be 8.2 and 7.9 nm, respectively. For $TiO_{2-x}$, the measured crystallite size is consistent with the expected size of 7 nm assuming that each 47 nm nanopore in the PDMC template was fully preloaded with TG precursor before being transformed into $TiO_{2-x}$. Thus, in some embodiments, the PDMC template plays at least two crucial roles: it controls the size of synthesized $TiO_{2-x}$ nanoparticles, preventing them from growing beyond the predefined size (in this case 7 nm); and by keeping the $TiO_{2-x}$ nanoparticles small, the template prevents the nanoparticles from converting from catalytically-active anatase phase to catalytically-inert rutile phase even after high temperature pyrolysis treatment (800° C.). The $TiO_{2-x}$ nanoparticles do not convert into rutile phase, because an anatase phase is more stable for small $TiO_2$ particles (<10 nm). Besides serving as a physical barrier preventing the $TiO_2$ nanoparticles from growing during pyrolysis of TGN at 800° C., the PDMC is instrumental in the conversion of the nanoparticles into reduced $TiO_{2-x}$.

$N_2$ porosimetry is used to investigate the pore structures and to determine the surface areas and pore sizes of PDMC, $TiO_{2-x}$/PDMC, $TiO_{2-x}$ and $TiO_2$—(H+C) (FIGS. 3E-H and 11). The $N_2$ adsorption/desorption isotherm of PDMC is type IV with type $H_2$ hysteresis loop, which is characteristic of a mesoporous material. Its BET surface area is 708 $m^2 g^{-1}$ and its BJH pore size distribution curve shows pores predominantly centered at ca. 43 nm, which correspond to the sizes of the colloidal silica templates. The $N_2$ adsorption/desorption isotherm of $TiO_{2-x}$/PDMC is also found to be type IV with type $H_2$ hysteresis loop. The surface area and pore size of $TiO_{2-x}$/PDMC are slightly lower, with a value of 440 $m^2$ $g^{-1}$ and 34 nm, respectively. Consistently, the pore volume of $TiO_{2-x}$/PDMC is also lower (1.63 $cm^3 g^{-1}$), compared with that of PDMC (2.00 $cm^3 g^{-1}$). These results indirectly corroborate the formation and the presence of titania inside the pores of PDMC, in line with the TEM images discussed earlier. It is worth adding here that a substantial amount of small mesopores and micropores (ca. 2 nm in size) is also found in both materials (see FIGS. 3F and 11). In the case of $TiO_{2-x}$, the surface area is 99 $m^2/g$, the pore volume is 0.23 $cm^3/g$, and the average pore diameter is 8.6 nm. The surface area and porosity of the corresponding control titania material, $TiO_2$—(H+C), is also obtained and compared with those of the other materials (see Table 1).

TABLE 1

Structural properties of PDMC, $TiO_{2-x}$/PDMC, $TiO_{2-x}$ and $TiO_2$—(H + C).[a]

| Materials | BET Surface Area (m$^2$ g$^{-1}$) | Average Pore Size (nm) | Pore Volume (cm$^3$ g$^{-1}$) |
|---|---|---|---|
| PDMC | 708 | 43 | 2.00 |
| $TiO_{2-x}$/PDMC | 440 | 34 | 1.63 |
| $TiO_{2-x}$ | 99 | 8.6 | 0.23 |
| $TiO_2$—(H + C) | 116 | 8.3 | 0.31 |

[a]Calculated based on the data in the adsorption branch of $N_2$ adsorption/desorption isotherms.

Figures 12A, 12B, 12C, 12D, 12E, 12F:
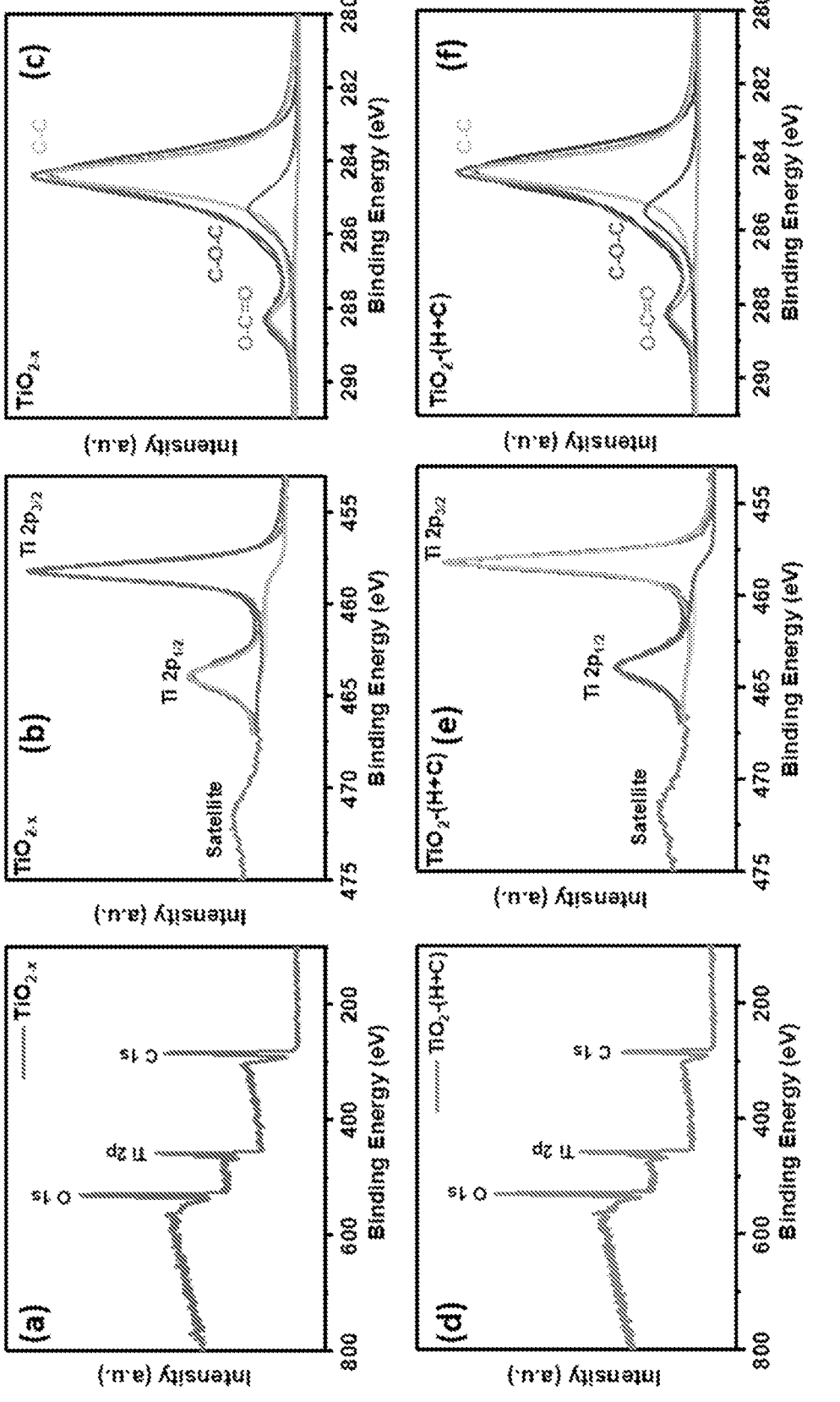
FIGS. 12A-12F illustrate XPS (X-ray photoelectron) survey spectra and high-resolution XPS spectra of C-1s peaks and Ti-2p peaks of $TiO_2$—(H+C) and $TiO_{2-x}$ materials.

X-ray photoelectron spectroscopy (XPS) was used to determine the chemical composition of the materials (FIGS. 12A-12F). The XPS survey spectra of $TiO_2$—(H+C) and $TiO_{2-x}$ reveal that both materials are composed of Ti, O and C. Peaks corresponding to N are not seen in the survey spectrum of $TiO_{2-x}$, indicating the absence of N dopants in this material. The presence of C in both materials is mainly due to the adventitious hydrocarbon species present on them (FIGS. 12C and 12F). The binding energy positions of Ti $2p_{3/2}$ and Ti $2p_{1/2}$ are observed at 458.2 and 463.9 eV, respectively. The splitting value between Ti $2p_{3/2}$ and Ti $2p_{1/2}$ is ca. 5.7 eV (FIGS. 12B and 12E), which is characteristic value of $TiO_2$. These results indicate that the yellowish color in $TiO_{2-x}$ is not caused by possible C and N dopant atoms, unlike the colors of other colorful $TiO_2$ materials.

Figures 4A, 4B, 4C:
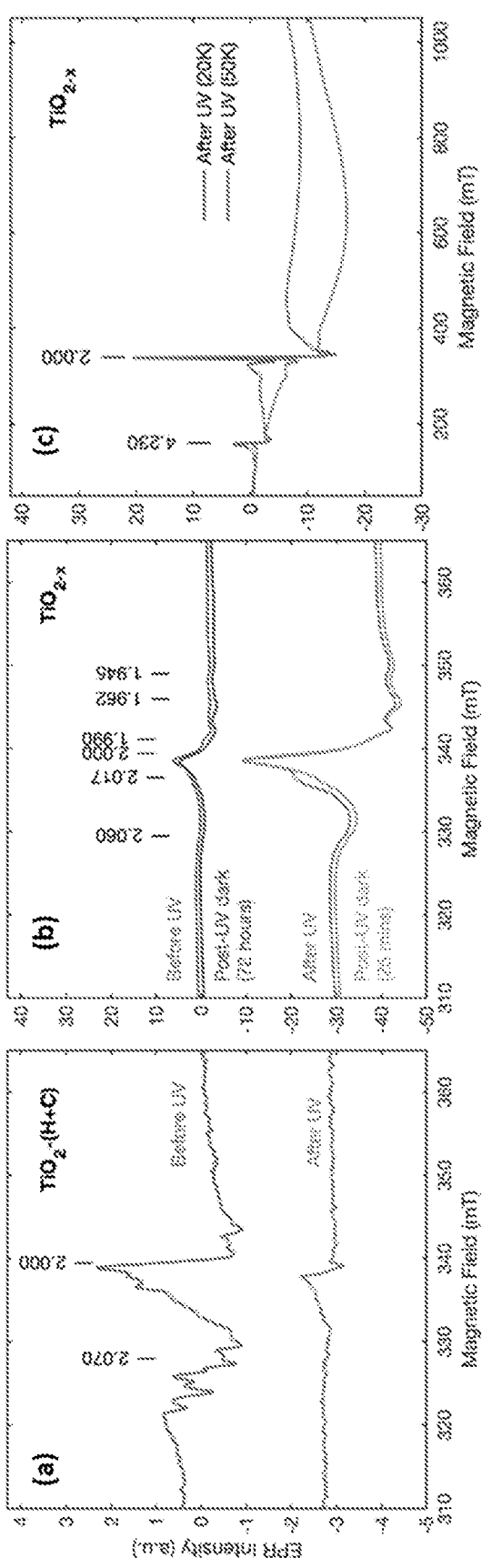
FIGS. 4A-4C illustrate electron paramagnetic resonance (EPR) characterization of the $TiO_2$-derived materials: EPR spectra of (FIG. 4A) $TiO_2$—(H+C) and (FIG. 4B) $TiO_{2-x}$ measured before (blue trace) and after (red trace) UV irradiation. Two additional spectra shown in (FIG. 4B) are for $TiO_{2-x}$ that is dark adapted for 25 min (green trace) or 72 h (purple trace) at room temperature after UV illumination. The spectra are vertically shifted for clarity. Vertical lines, marked with their g-factor values, identify the main peaks resolved in the EPR spectra for: $Cu^{2+}$ impurities (2.060-2.070); holes trapped on (undercoordinated) 0 atoms (2.017); negatively-charged O vacancies and weakly-localized electrons (polarons) (2.000); bulk $Ti^{3+}$ centers (1.990 and 1.962); and surface $Ti^{3+}$ centers (1.945). EPR experimental conditions are: temperature, 20 K; microwave frequency, 9.5 GHz; microwave power, 0.2-2 mW; and modulation amplitude, 0.5-1 mT.

Probing Long-Lived Charge Carriers of $TiO_{2-x}$. Electron paramagnetic resonance (EPR) is used to further clarify the difference between $TiO_2$—(H+C) and $TiO_{2-x}$ and also to determine the nature of mid-gap defect states responsible for the observed UV-Vis absorption edge shift in $TiO_{2-x}$ (and its yellowish appearance). Both samples are measured several times: before and after UV irradiation, and then after dark adaptation at room temperature following the UV irradiation (FIGS. 4A-4C). Several peaks resolved in the EPR spectra are identified based on their g-factor values. The signal at g=2.017 is believed to be from holes trapped at undercoordinated oxygen atoms (O$^-$ centers) and possibly hydroxyl groups on the surfaces of $TiO_2$. The signal at g=2.000 has several overlapping contributions, including electrons trapped at oxygen vacancies and weakly-localized electrons (polarons) associated with Ti$^{3+}$ centers in bulk and at surfaces of the crystallites. The signals at g=(1.990, 1.962) correspond to bulk Ti$^{3+}$ centers, and the broad signal at g=1.945 is from surface Ti$^{3+}$ centers.

As seen in FIG. 4A, all EPR signals of $TiO_2$—(H+C) are weak before its exposure to UV light, and the signals are further suppressed after the UV exposure. Based on the signal intensity at g=2.000, and considering the average crystallite grain size of ca. 8 nm as determined from our XRD data, the average number of spin defects per crystallite in $TiO_2$—(H+C) before the UV exposure is estimated to be between 0.02-0.04. This defect count includes ionized oxygen vacancy centers and also weakly-localized electrons (polarons) in bulk and at surface of $TiO_2$—(H+C) crystallites. After the UV exposure the spin defect number in $TiO_2$—(H+C) reduces essentially to zero, indicating that all paramagnetic defects are now fully ionized by trapping electrons or holes generated during the UV illumination and that they are converted into their EPR-invisible states.

The EPR signals are noticeably stronger in $TiO_{2-x}$ (FIG. 4B). Note that the vertical (intensity) scale in FIG. 4B is ten times larger than that for $TiO_2$—(H+C) in FIG. 4A. When measured in the dark, the spin count number, for the g=2.000 line, gives on average 0.2 spin defects per a crystallite grain in $TiO_{2-x}$, a remarkable 5-10 increase over what is found for $TiO_2$—(H+C). After the UV exposure the defect number in $TiO_{2-x}$ increases even further to about 0.85 spin defects per crystallite, again in marked contrast to $TiO_2$—(H+C) where the number of spin defects decreases after the UV exposure. The high density of spin defects in the dark $TiO_{2-x}$, and its additional four times increase after the UV exposure (almost to the level of one defect per crystallite), point to a greatly increased density of 0 vacancies and shallow-trap defects (e.g. undercoordinated Ti$^{3+}$ and O$^-$ species) in reduced $TiO_{2-x}$. A small fraction of these defects (0.2 defects per crystallite) is already ionized and EPR-visible in the sample kept in the dark. Even a larger fraction (0.85 defects per crystallite) is converted to the ionized, EPR-visible states, by trapping photogenerated electrons and holes, after the UV exposure. These mid-gap defects, including 0 vacancies and undercoordinated Ti$^{3+}$ and O$^-$ sites in the bulk and at surface of the material, are also the most probable causes of the red shift in the absorption spectra of $TiO_{2-x}$ and its yellowish color.

To test the stability of photogenerated electron/hole charge defects in $TiO_{2-x}$, the UV-irradiated samples were warmed up and kept in the dark at room temperature for varied periods of time, freezing them again and remeasuring their EPR spectra. The room temperature dark adaptation for 25 min (the green trace in FIG. 4B) did not produce any visible changes in the EPR spectrum as compared to the one measured immediately after the UV irradiation (the red trace in FIG. 4B). This indicates that all photogenerated electron/hole charge states are stable and undergo no charge recombination on that time scale even at room temperature. However, the dark adaptation for 72 h (the purple trace) gives rise to a complete recovery of the spectrum to what is originally obtained for the sample before any UV exposure (the blue trace in FIG. 4B), with all photogenerated charge states being fully recombined to their original dark states. The long lifetimes of photogenerated electron/hole traps in our $TiO_{2-x}$ and in certain non-limiting embodiments their slow recombination even at room temperature can be an important factor explaining the enhanced photocatalytic activity of $TiO_{2-x}$ toward $CO_2$ reduction that is discussed below.

In addition to the EPR signals around g-factor 2.000 as discussed above, $TiO_{2-x}$ after UV irradiation also develops a broad baseline signal spanning from 100 to 1000 mT, as shown in FIG. 4C. This broad signal is not observed in $TiO_2$—(H+C), neither before nor after UV irradiation. Notably, the intensity of this broad signal increases when the temperature increases from 20 to 50 K; the behavior is contrary to what would be expected from a conventional EPR signal. Indeed, all other peaks seen in the same EPR spectra in FIG. 4C show a consistent decrease in their intensities by~2.5x, when temperature changes from 20 to 50 K. The broad linewidth, the significant signal intensity and the atypical temperature dependence, all taken together point to the unconventional origin of this broad baseline signal in $TiO_{2-x}$.

In certain non-limiting embodiments, this broad signal originates from weakly-localized electrons (polarons), produced during UV irradiation and trapped in bulk and at surface of $TiO_{2-x}$. These electrons/holes conductively couple to a microwave electrical field, resulting in electrically-driven spin resonance. The existence of such electron/hole states, with shallow trap potentials and low energy hopping barriers, in reduced $TiO_{2-x}$ was previously predicted in DFT calculations by other researchers. These shallow electron/ hole states remain fully localized at low temperatures (below 20 K) and their conductive coupling to microwave electric fields is therefore mostly suppressed. However, at higher temperatures exceeding the electron confining energy (above 10 K in our case), the shallow electrons/holes become mobile, being involved in a charge hoping and a cyclotron motion; and, through this motion they conductively couple to electric microwave field causing strong microwave absorption and resulting in a broad spectral baseline signal, as observed in the EPR spectra in FIG. 4C. Broad baseline EPR signals with similar spectral line shapes were observed for conduction and weakly-localized electrons in Si/SiGe heterostructures where these signals were ascribed to the cyclotron resonance microwave absorption. The stability of this broad baseline EPR signal in the present $TiO_{2-x}$ is also tested by warming the UV-irradiated sample to room temperature and by observing that the signal remains stable for the first 30 minutes. The signal completely decays down only after 72 h in the dark at room temperature.

Blinking Properties of $TiO_{2-x}$/PDMC under Electron Beam. The $TiO_{2-x}$ material shows unusual blinking properties under exposure to slow electron beams during TEM imaging (see FIG. 5). This blinking behavior appears to be due to charge-discharge processes of electrons being trapped and then released from some deep traps in $TiO_{2-x}$ crystallites. The blinking persists indefinitely for as long as the sample is kept under electron beam. This is an unusual phenomenon, because most materials during TEM imaging acquire their charged state very quickly (within milliseconds) and then show no oscillations between bright/dark states. Images are taken while some of the particles are in bright state and others in dark state (FIGS. 5A and 5B).

Figures 5A, 5B, 5C:
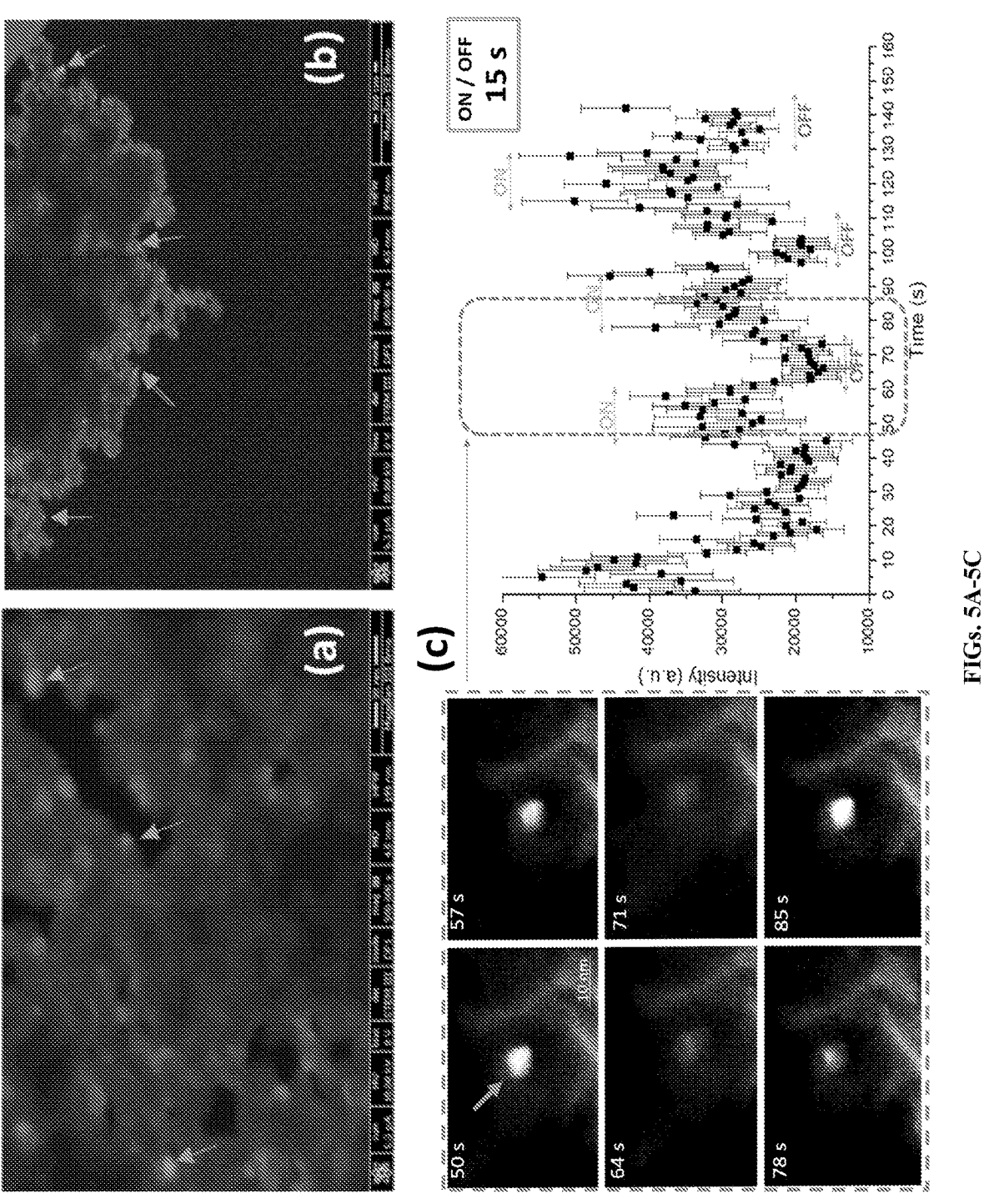
FIGS. 5A-5C illustrate brightness blinking of $TiO_2$ nanocrystallites under electron beam.

The blinking time dependence for one of the $TiO_{2-x}$ nanoparticles is shown in FIG. 5C. The bright/dark (ON/OFF) switching takes place on ca. 15 s time scale. Importantly, the brightness ON/OFF intensities remain approximately the same even after a few switching cycles, indicating that the charging/discharging processes probably involve addition/removal of only one electron. The blinking frequency between the ON/OFF states was examined for different crystallites and at different electron beam intensities, and the frequency was found to be similar in all.

Photocatalytic Reduction of $CO_2$ by $TiO_{2-x}$ and Control Materials. A 200 mL-size home-made Pyrex reactor was used to perform the photocatalytic $CO_2$ reduction over the $TiO_{2-x}$ materials (or control materials) at room temperature and at atmospheric pressure. In one embodiment, prior to the test, 50 mg of the $TiO_{2-x}$ material was mixed with 10 mL of deionized water, and the mixture was poured into the reactor. The mixture was then ultrasonically dispersed for 30 min, and the solvent in it was allowed to evaporate at 80° C. for 2 h. After a thin film of the solid sample formed on the bottom of the reactor, the reactor was sealed off. In order to create anaerobic conditions in the reactor, the air in it was removed by blowing $N_2$ gas into the reactor for 30 min. The reactants used as a source of carbon (viz. $CO_2$) and hydrogen (viz. $H_2O$) were generated in situ by letting $NaHCO_3$ (0.1 g, which was added into the reactor before sealing it off) and 2 M sulfuric acid (0.3 mL which was purged into the reactor using a syringe) react for 30 min, before turning on the UV light irradiation. A 300 W simulated solar Xe arc lamp was positioned 10 cm above the photocatalytic reactor and used as the source of light. After 1 h of light irradiation, 1 mL of the gas sample was taken from the reactor and analyzed by gas chromatograph (GC-2014C, Shimadzu, Japan) equipped with a flame ionization detector (FID). Blank experiments were also performed without the presence of $CO_2$ in the reactor and/or without exposing the reactor to irradiation. These control experiments allowed one to check if any of the products could be generated without photocatalytic processes and without the presence of $CO_2$.

Figure 6:
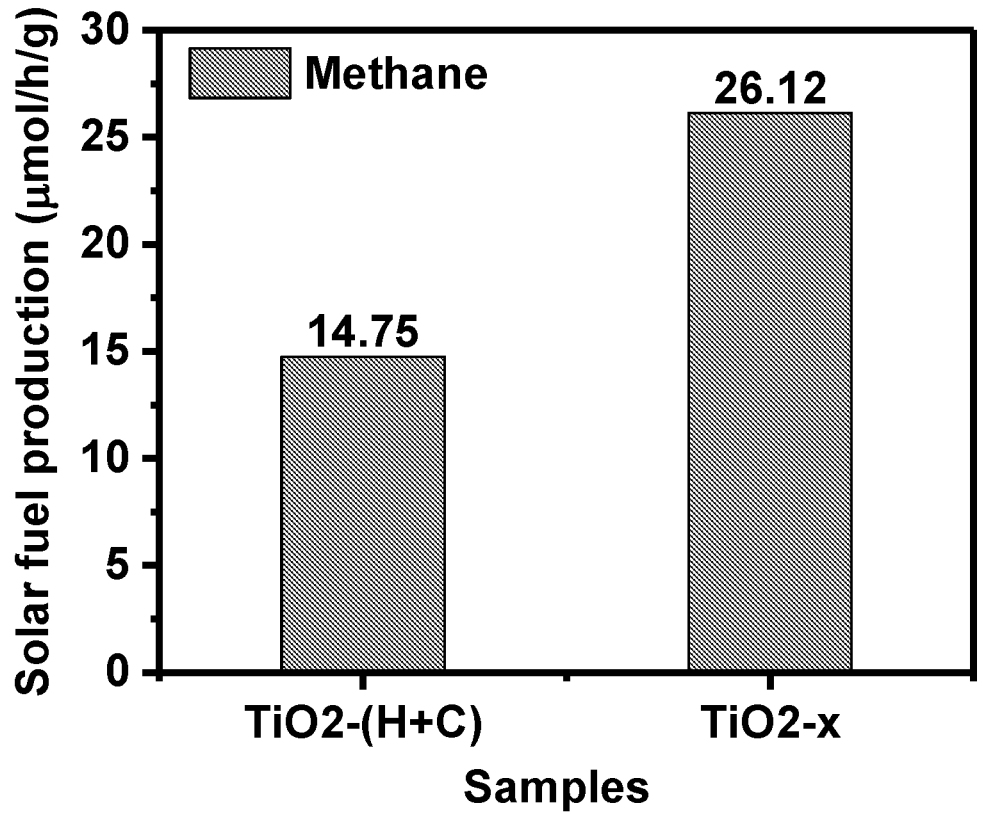
FIG. 6 illustrates rates of photocatalytic production of $CH_4$ from $CO_2$ reduction with $H_2O$ over $TiO_2$—(H+C) and $TiO_{2-x}$ materials.
Figures 7A, 7B, 7C, 7D, 7E, 7F:
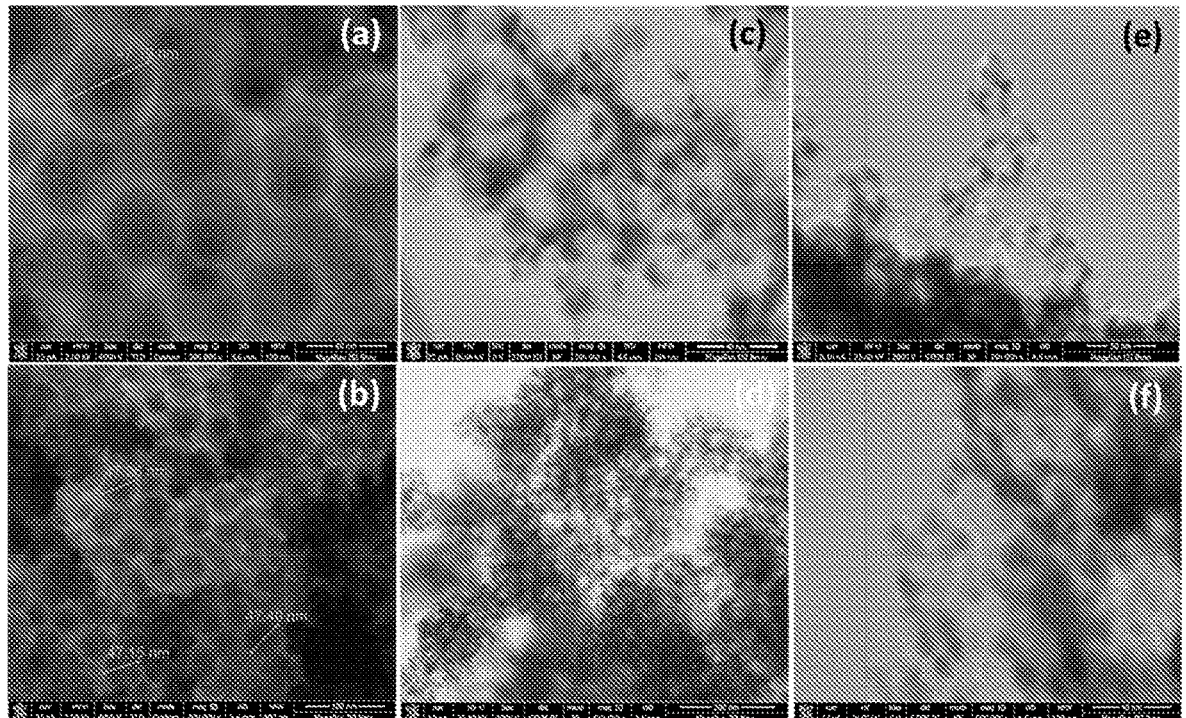
FIGS. 7A-7F illustrate STEM images of (FIGS. 7A-7B) PDMC, (FIGS. 7C-7D) $TiO_{2-x}$/PDMC, and (FIGS. 7E-7F) $TiO_{2-x}$ materials.
Figure 8:
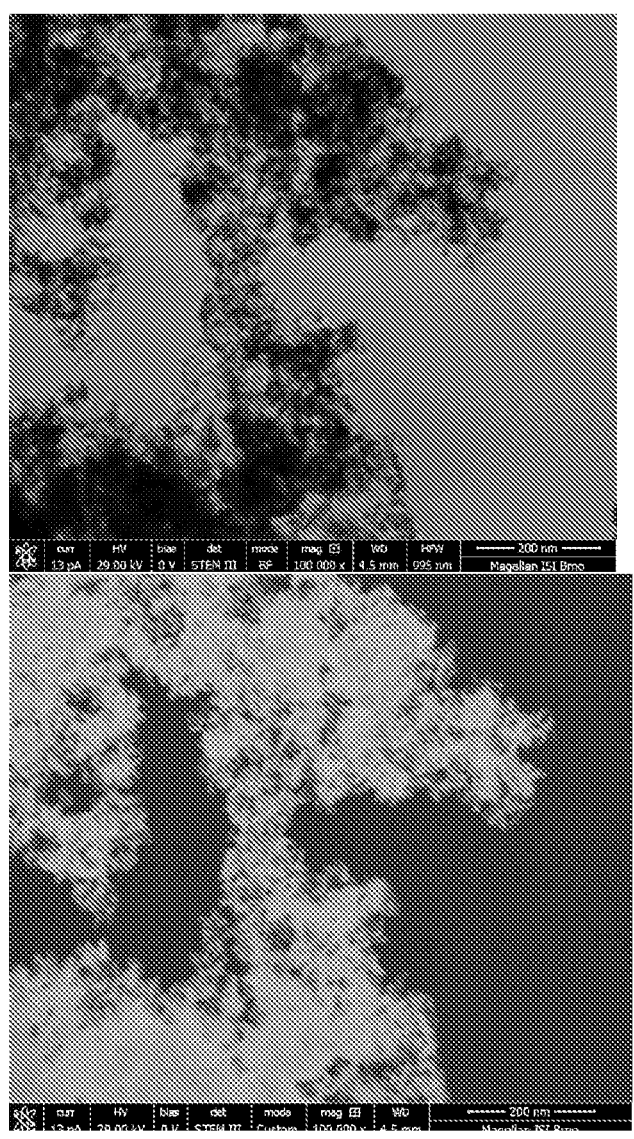
FIG. 8 illustrates dark field and bright field STEM image of $TiO_{2-x}$ obtained using 29 keV electron beam.
Figure 9:
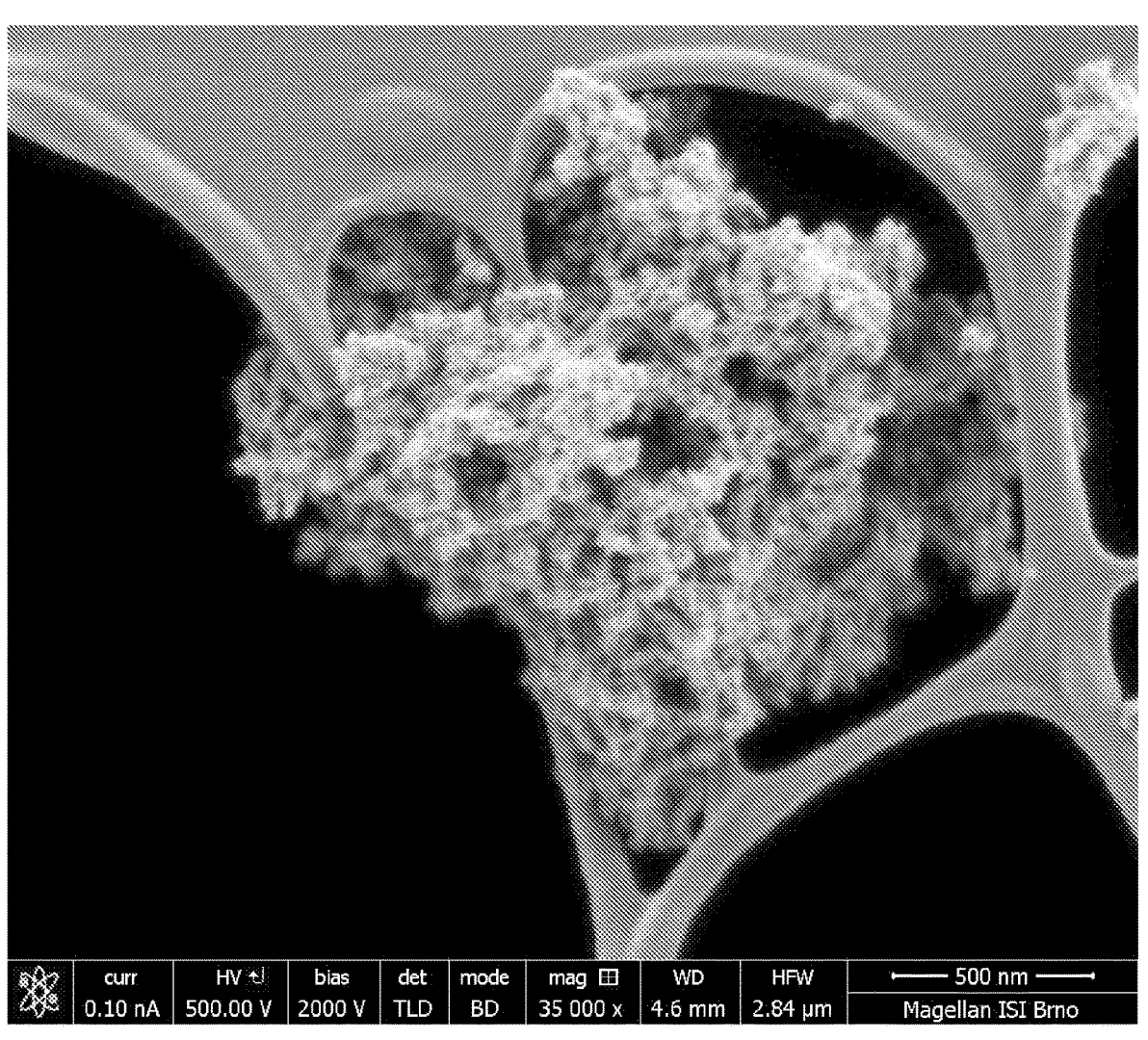
FIG. 9 illustrates an SEM image of $TiO_{2-x}$ obtained using low energy electron beams (0.5 keV).

Considering its highly nanoporous structure and large surface area, as well as its improved optical absorption properties and long-lived charge separation capability, the $TiO_{2-x}$ material is expected to be proficient in photo-catalyzing various reactions. With this in mind, the photocatalytic activity of $TiO_{2-x}$ as well as of the control material $TiO_2$—(H+C) is examined in the $CO_2$ reduction reaction (FIG. 6). No hydrocarbon products are detected in the reaction chamber with $TiO_{2-x}$ or $TiO_2$—(H+C) in the absence of $CO_2$, even after prolonged UV irradiation, indicating a high stability of both materials. In the presence of $CO_2$, $H_2O$ and light, both materials yield a hydrocarbon product ($CH_4$). The rate of $CH_4$ production from the reaction over $TiO_{2-x}$ and $TiO_2$—(H+C) is 26.12 mol h$^{-1}$ g$^{-1}$ and 14.75 mol h$^{-1}$ g$^{-1}$, respectively (FIG. 6). Since both materials possess similar surface areas, porosities, phase compositions, crystallinity and crystallite sizes, the enhanced photocatalytic activity of $TiO_{2-x}$ is most likely due to presence of high concentrations of O vacancies and also $Ti^{3+}$ and $O^-$ associated shallow electron/hole trap centers (as evidenced from our EPR results). These shallow electron/hole centers can serve both as trapping sites for photo-generated electrons/holes and also as catalytical binding centers for substrate $CO_2$ and $H_2O$ (or —OH species) on the $TiO_{2-x}$ surfaces, thus enhancing the charge separation efficiency and the overall photocatalytic activity. The photocatalytic activity of the $TiO_{2-x}$ described herein is comparable or better than many other notable photocatalytic materials reported recently, Table 2.

TABLE 2

Comparisons of the performance of the $TiO_{2-x}$ photocatalyst reported herein for $CO_2$ reduction with those of different notable $TiO_2$-based photocatalysts recently reported in the literature.

| Photocatalysts | Light Source | Major Products | Yield ($\mu$mol h$^{-1}$ g$^{-1}$) |
|---|---|---|---|
| $TiO_2$ nanoparticles | 8 W Hg lamp | $CH_4$, $CH_3OH$ | ca. 0.4, 0.05 |
| Fluorinated $TiO_{2-x}$ | 300 W Xe lamp with an AM 1.5 filter | $CH_4$ | 1.63 |
| $Pd_7Cu_1$-loaded $TiO_2$ | 300 W Xe lamp with a 400 nm short-wave-pass cutoff filter | $CH_4$ | 19.6 |
| 3 wt. % CuO—$TiO_2$ hollow sphere | 40 W Hg UV lamp | $CH_4$ | 2.1 |
| 1.5 wt. % Ag—$TiO_2$ | 300 W Xe lamp | $CH_4$ | 11.2 |
| Au—Cu—$TiO_2$ | 1000 W Xe lamp | $CH_4$ | 44 |
| N-doped $TiO_2$ | Compact fluorescent integrated bulbs | $CH_4$ | 0.16 |
| N—$TiO_2$ | Full spectrum light irradiation | $CH_3OH$ | 20 |
| 45% CdS/$TiO_2$ | Hg lamp | $CH_4$ | ca. 0.5 |
| $TiO_{2-x}$ described herein | 300 W Xe lamp | $CH_4$ | 26.12 |

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

Enumerated Embodiments

The following exemplary embodiments are provided, the numbering of which is not to be construed as designating levels of importance:

Embodiment 1 provides a material comprising $TiO_{2-x}$, wherein the particle has a light absorption onset of about 400 nm to about 510 nm, and wherein x is a number ranging from 0.001 to 0.100.

Embodiment 2 provides the material of embodiment 1, wherein the $TiO_{2-x}$ is in an anatase phase.

Embodiment 3 provides the material of any one of embodiments 1-2, which does not substantially aggregate with a plurality of equivalent particles.

Embodiment 4 provides the material of any one of embodiments 1-3, which has an average pore size of about 2 to about 12 nm.

Embodiment 5 provides the material of any one of embodiments 1-4, which has an average pore size of about 12 to about 40 nm.

Embodiment 6 provides the material of any one of embodiments 1-5, which has a BET surface area of about 70 to about 110 $m^2$ $g^{-1}$.

Embodiment 7 provides the material of any one of embodiments 1-6, which has a pore volume of about 0.1 to about 0.3 $cm^3$ $g^{-1}$.

Embodiment 8 provides the material of any one of embodiments 1-7, which comprises at least one of optically-active mid-gap states related to oxygen vacancies or interstitial $Ti^{3+}$ species.

Embodiment 9 provides the material of any one of embodiments 1-8, wherein the interstitial $Ti^{3+}$ species comprises a plurality of under-coordinated $O^-$ groups.

Embodiment 10 provides a method of making a titanium oxide particle, the method comprising: contacting a titanium-containing compound with at least one polymer-derived mesoporous carbon (PDMC) material; and heating the titanium-containing compound and the PDMC at a temperature of about 500 to 1200° C. in an inert atmosphere to form titanium oxide particles.

Embodiment 11 provides the method of embodiment 10, wherein the titanium-containing compound comprises titanium glycolate.

Embodiment 12 provides the method of any one of embodiments 10-11, wherein the PDMC material comprises polymerized aniline.

Embodiment 13 provides the method of any one of embodiments 10-12, wherein the heating step comprises forming $TiO_{2-x}$ nanoparticles.

Embodiment 14 provides the method of any one of embodiments 10-13, further comprising calcining the $TiO_{2-x}$ nanoparticles and the PDMC in air.

Embodiment 15 provides the method of embodiment 14, wherein the calcining is at a temperature of about 450 to 650° C.

Embodiment 16 provides the method of any one of embodiments 14-15, wherein the calcining removes the PDMC and provides a titanium oxide material.

Embodiment 17 provides the method of embodiment 16, wherein the titanium oxide particle has at least one of the following characteristics: an average pore size of about 5 to about 12 nm, a BET surface area of about 70 to about 110 $m^2$ $g^{-1}$, a pore volume of about 0.1 to about 0.3 $cm^3$ $g^{-1}$.

Embodiment 18 provides the method of any one of embodiments 16-17, wherein the titanium oxide material has a light absorption onset of about 400 nm to about 510 nm.

Embodiment 19 provides a method of reducing carbon dioxide, the method comprising: contacting a gas comprising $CO_2$ with the material of any of claims 1-8 in the presence of light; and reducing the $CO_2$ to provide $CH_4$.

Embodiment 20 provides the method of embodiment 19, wherein the $CH_4$ production rate is about 16 to 35 $\mu mol$ $h^{-1}$ $g^{-1}$.

Embodiment 21 provides the method of any one of embodiments 19-20, wherein the light comprises ultraviolet radiation.

What is claimed is:

1. A material comprising $TiO_{2-x}$ nanoparticles, wherein:
the material has a light absorption onset of about 400 nm to about 510 nm;
x is a number ranging from 0.001 to 0.100;
the nanoparticles have a substantially uniform size;
the nanoparticles have an average size of about 5 to about 12 nm; and
the material has an average pore size of about 5 to about 12 nm.

2. The material of claim 1, wherein the $TiO_{2-x}$ is in an anatase phase.

3. The material of claim 1, which does not substantially aggregate with a plurality of equivalent particles.

4. The material of claim 1, which has a BET surface area of about 70 to about 110 $m^2$ $g^{-1}$.

5. The material of claim 1, which has a pore volume of about 0.1 to about 0.3 $cm^3$ $g^{-1}$.

6. The material of claim 1, which comprises at least one of optically-active mid-gap states related to oxygen vacancies or interstitial $Ti^{3+}$ species.

7. The material of claim 6, wherein the interstitial $Ti^{3+}$ species comprises a plurality of under-coordinated $O^-$ groups.

8. A method of reducing carbon dioxide, the method comprising:
contacting a gas comprising $CO_2$ with the material of claim 1 in the presence of light; and
reducing the $CO_2$ to provide $CH_4$.

9. The method of claim 8, wherein at least one of the following applies:
the $CH_4$ production rate is about 16 to 35 $\mu mol$ $h^{-1}$ $g^{-1}$;
the light comprises ultraviolet radiation.

* * * * *